US00PP28682P3

(12) United States Plant Patent
Layt

(10) Patent No.: US PP28,682 P3
(45) Date of Patent: Nov. 21, 2017

(54) ***HARDENBERGIA VIOLACEA* PLANT NAMED 'HB2'**

(50) Latin Name: *Hardenbergia violacea*
Varietal Denomination: HB2

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 0 days.

(21) Appl. No.: 15/330,436

(22) Filed: Sep. 21, 2016

(65) Prior Publication Data

US 2017/0094875 P1 Mar. 30, 2017

Related U.S. Application Data

(60) Provisional application No. 62/232,750, filed on Sep. 25, 2015.

(51) Int. Cl.
*A01H 5/02* (2006.01)

(52) U.S. Cl.
USPC ..... Plt./323

(58) Field of Classification Search
USPC ..... Plt./323
See application file for complete search history.

*Primary Examiner* — Annette H Para
(74) *Attorney, Agent, or Firm* — Samuel R. McCoy, Jr.

(57) ABSTRACT

'HB2' is a distinctive variety of *Hardenbergia violacea* which is characterized by a dense and compact shrub habit, a short plant height and small, ovate foliage.

1 Drawing Sheet

Latin name of the genus and species: The Latin name of the genus and species of the novel variety disclosed herein is *Hardenbergia violacea.*

Variety denomination: The inventive variety of *Hardenbergia violacea* disclosed herein has been given the variety denomination 'HB2'.

BACKGROUND OF THE INVENTION

*Hardenbergia violacea* is a flowering vine or subshrub native to Australia which belongs to the pea family, Fabaceae. Flowers are typical of the pea family and range in color from white to violet to pink. Foliage is usually dark green and leathery. *Hardenbergia* can be found in production throughout Australia and the United States. The present invention relates to a new and distinct perennial variety of *Hardenbergia violacea,* which has been given the variety denomination of 'HB2'. Its market class is PLT/226. 'HB2' is intended for use in landscaping and as a decorative plant.

Parentage: The *Hardenbergia violacea* variety 'HB2' is the result of a selection process carried out at a commercial breeding facility in Clarendon, New South Wales, Australia from 2011 to 2012. Said selection process involved openly-pollinated seedlings of *Hardenbergia violacea* 'Mini Haha' (unpatented), the seed parent, and *Hardenbergia violacea* 'HB1' (unpatented), believed to be the pollen parent. In the spring of 2011, 'Mini Haha' and 'HB1' plants were grown in pairs, in 200 mm nursery pots, with one pot of each cultivar placed next to the other. Two such pairs were grown simultaneously with approximately 100 meters separating them. Said pairs were allowed to openly pollinate and the resulting seed was subsequently harvested from the 'Mini Haha' plants in early summer of that same year. Said seeds were then sown, with a small number of five seedlings germinating. Of the five seedlings, four expressed a phenotype that was the same or very similar to the seed parent plant. By contrast, the fifth seedling exhibited a denser, ball-shaped growth habit, a smaller leaf, and a different leaf shape. This seedling was isolated for further evaluation and confirmation of the stability of the initially observed characteristics. The final selection was made after flowering in 2012 and the new cultivar was given the denomination 'HB2'.

Asexual Reproduction: 'HB2' was first propagated asexually by stem cuttings at the same commercial breeding facility in Clarendon, New South Wales, Australia in 2012 and has since gone through five successive cycles of vegetative propagation. The distinctive characteristics of the inventive 'HB2' variety are stable from generation to generation; plants of the variety produced by asexual reproduction maintain the distinguishing characteristics of the original plant.

SUMMARY OF THE INVENTION

The following traits have been repeatedly observed and represent the characteristics of the new cultivar. The characteristics in combination distinguish 'HB2' as a distinct cultivar of *Hardenbergia violacea.*

1. 'HB2' exhibits a compact and very dense shrub growth habit; and
2. 'HB2' exhibits a rotund, ball plant shape; and
3. 'HB2' exhibits a short plant height; and
4. 'HB2' exhibits an ovate leaf shape; and
5. 'HB2' exhibits a small leaf.

BRIEF DESCRIPTION OF THE FIGURES

The accompanying FIGURE illustrates as true as is reasonably possible to obtain in color photographs of this type, an exemplary 'HB2' specimen, approximately 3 years of age, grown at a commercial breeding facility in Clarendon, New South Wales, Australia.

BOTANICAL DESCRIPTION OF THE PLANT

The following is a detailed botanical description of a new and distinct variety of a *Hardenbergia violacea*, known as 'HB2'. Plant observations were made on plants grown in Clarendon, New South Wales, Australia. Unless indicated otherwise, the descriptions disclosed herein are based upon observations made from 3 year old field-grown plants. Plants were maintained with granular slow release fertilizer and occasional, infrequent overhead irrigation. No pest and disease measures were taken.

Those skilled in the art will appreciate that certain characteristics will vary with older or, conversely, younger plants. 'HB2' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart,* The Royal Horticultural Society, London, 2001 edition. Note that generic color descriptions such as 'purple' do not exist in the R.H.S. charts and the corresponding R.H.S. colors are quoted.

A botanical description of 'HB2' and comparisons with other varieties of *Hardenbergia violacea* are provided below.

Plant description:

*Plant habit.*—Rotund, shrub habit, free of any twining; compact and dense.

*Height.*—500 mm.

*Width.*—300 mm.

*Hardiness.*—USDA Zones 9 to 11.

*Environmental tolerances.*—Prefers full to filtered sun; drought tolerant.

*Pest and disease susceptibility or resistance.*—In common with the species, none of note.

*Propagation.*—Propagation is accomplished using softwood stem cuttings. Roots well without rooting compound or hormone.

*Time to develop roots.*—4 to 5 weeks.

*Crop time.*—Approximately 10 weeks to produce a rooted cutting; 8 months are needed to produce a 20-centimeter container with plant in flower, starting from a rooted cutting.

Roots:

*General description.*—Tap root.

Stem:

*Branching and habit.*—Strong basal and axillary branching habit; freely branching. Branch attitude is semi-erect.

*Number of stems.*—Numerous; more than 30.

*Stem strength.*—Medium.

*Cross-section.*—Round.

*Stem color, immature.*—Closest to Greyed-Red Group 178A.

*Stem color, mature.*—Yellow-Green Group 146A.

*Stem diameter.*—1.6 mm, midway along mature stems.

*Stem surface.*—Mature stems are woody, hard and smooth.

*Internode length.*—11 mm, midway along mature stems.

*Tendrils.*—Absent.

Foliage:

*Arrangement.*—Alternate.

*Attachment.*—Petiolate.

*Shape.*—Ovate.

*Apex.*—Mucronate.

*Base.*—Obtuse.

*Dimensions.*—33 mm long and 15.5 mm wide.

*Margins.*—Entire.

*Texture.*—Smooth and glabrous.

*Color, juvenile foliage.*—Adaxial surface — Greyed-Orange Group 166A. Abaxial surface — Greyed-Orange Group 166A.

*Color, mature foliage.*—Adaxial surface — Green Group 139A. Abaxial surface — Green Group 137A.

*Venation.*—Reticulate.

*Vein color, adaxial surface.*—Green Group 138B.

*Vein color, abaxial surface.*—Green Group 138C.

*Petiole.*—Approximately 10 mm long and 1 mm wide; color is Green Group 138B.

*Stipules.*—Laminar; glabrous; color is Greyed-Red Group 178A; glabrous; length is approximately 2.5 mm.

Inflorescence:

*Type.*—Numerous axillary racemes.

*Natural flowering season.*—In the northern hemisphere, mid-February through April.

*Quantity of flowers.*—Up to 15 flowers on each inflorescence.

*Dimensions.*—55 mm long and 25 mm wide.

*Peduncle.*—Attitude — Erect. Dimensions — 30 mm long and 1.5 mm wide. Texture — Smooth and glabrous. Color — A combination of Yellow-Green Group 146A and Greyed-Purple 187D.

Bud:

*Bud shape.*—An oblong sphere with a falcate profile.

*Bud dimensions.*—Approximately 6 mm long and 3 mm wide.

*Bud color.*—Violet Group N88A.

*Rate of bud opening.*—Rapid.

Flower:

*General description.*—Flower type — Complete; zygomorphic. Flower shape — Papilionate. Aspect — Outward. Persistence — Low. Fragrance — Nonfragrant.

*Calyx.*—General — Fused with five sepal lobes, forming a cup. Sepals — Shape — Deltoid. Apex — Acute. Margins — Entire. Length of sepal lobes — 2.5 mm. Color, immature — Greyed-Green Group 191A. Sepal texture — Slightly rough.

*Corolla.*—Petal arrangement — Typical pea type flower with a standard petal, a wing petal and two keel petals; petals fused. Dimensions — 12.5 mm across, at the widest point, with a depth of 10 mm from base of the calyx to the apex of the keep petals. Standard petal — Shape is rounded; margins are entire. Color is Purple-Violet Group 84C. Markings present near base of standard petal along midrib; color is Yellow-Green Group 149A. Surfaces are matte and glabrous. Winged petal — Shape is obovate; apex is broad and round; base is acute; margins are undulate. Color of both surfaces is Purple Group 82A. Surfaces are matte and glabrous. Keel petal — Shape is falcate; apex is round; base is acute; margins are entire. Color of both surfaces is Purple Group 82A. Surfaces are matte and glabrous.

*Pedicel.*—Dimensions — Approximately 5 mm long and 1 mm wide. Texture — Smooth and glabrous. Color — Greyed-Purple Group 186D.

Reproductive organs:

*Stamens.*—Quantity — 10. Filament — Diadelphous; color is closest to Green-White Group 157D. Overall length is approximately 4.5 mm long. Anther dimensions — Approximately 1.0 mm long by 0.75 mm wide. Anther color — A combination of Yellow-Green Group 150C and 151D.

*Pollen.*—Amount of pollen — Low. Pollen color — Green-White Group 157D.

*Pistil (if present).*—Quantity — One. Dimensions — 5 mm long and approximately 0.5 mm wide. Stigma — Green-White Group 157D. Style — Short; 1 to 2 mm long.

*Ovary.*—Superior; 25 mm long and 8 mm wide.

Fruit and seed production:

*Fruit.*—Legume pod; approximately 25 mm long and 8 mm wide.

*Seed.*—Black Group 202A; hard; hard, approximately 2 to 3 mm long; kidney shaped.

Comparison With the Parents

'HB2' may be distinguished from its seed parent and closest known commercial comparator, 'Mini Haha', by the following combination of characteristics:

1. 'HB2' exhibits a rotund growth habit, whereas 'Mini Haha' exhibits an erect growth habit.
2. 'HB2' exhibits a small leaf, whereas 'Mini Haha' exhibits a leaf of medium size for the genus.
3. 'HB2' exhibits an ovate leaf shape, whereas 'Mini Haha' exhibits an oblong leaf shape.

'HB2' may be distinguished from its pollen parent, 'HB1', by the following combination of characteristics:

1. 'HB2' exhibits a short plant height of approximately 50 cm tall, whereas 'HB1' can grow to approximately 100 cm tall.
2. 'HB2' exhibits a general plant width of approximately 30 cm, whereas 'HB1' exhibits a plant width of 60 cm.
3. 'HB2' exhibits small, ovate foliage whereas 'HB1' exhibits larger, oblong foliage.

That which is claimed is:

1. A new and distinct variety of *Hardenbergia violacea* plant named 'HB2', substantially as described and illustrated herein.

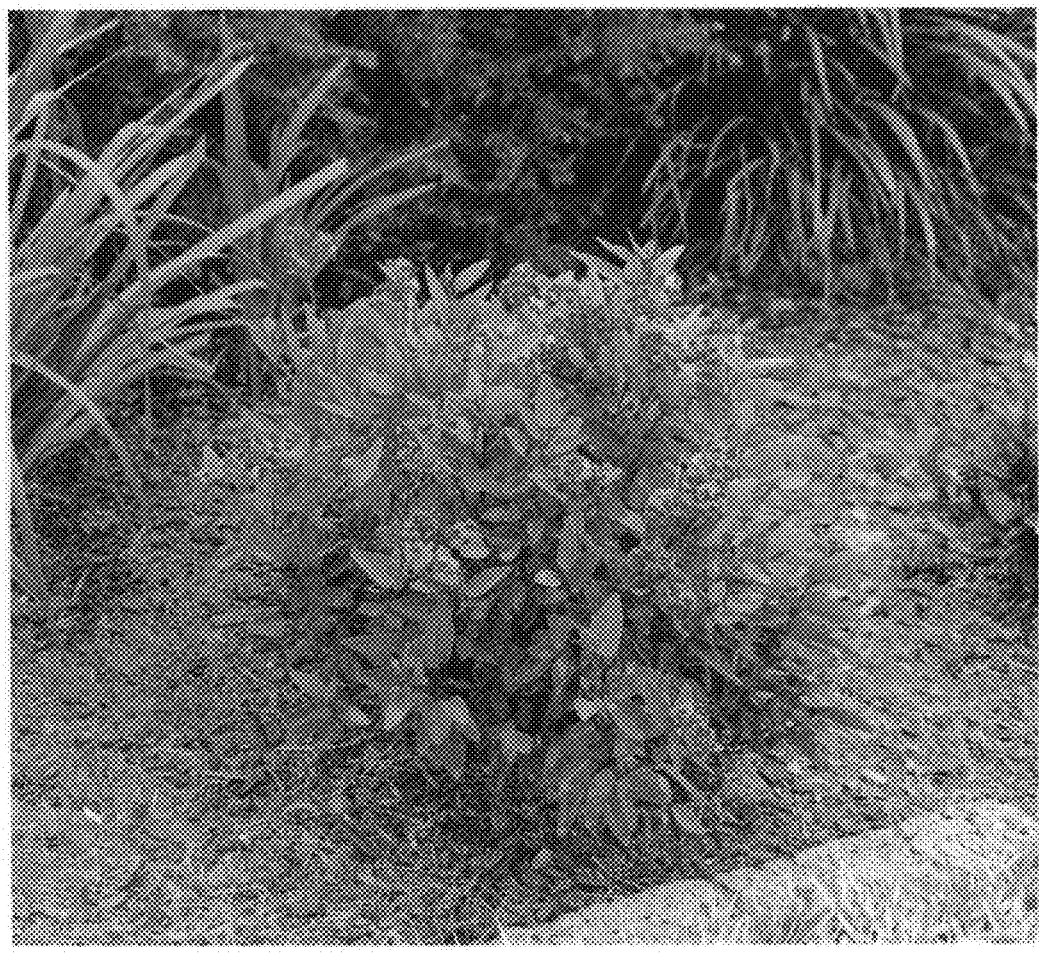

* * * * *